US00PP14207P29

(12) United States Plant Patent
Danziger

(10) Patent No.: US PP14,207 P2
(45) Date of Patent: Oct. 7, 2003

(54) IMPATIENS PLANT NAMED 'DANCHESPARKRD'

(50) Latin Name: *Impatiens walleriana*
Varietal Denomination: Danchesparkrd

(75) Inventor: Gabriel Danziger, Nir-Zvi (IL)

(73) Assignee: Danziger - "DAN" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 10/230,313

(22) Filed: Aug. 29, 2002

(51) Int. Cl.[7] ..... A01H 5/00
(52) U.S. Cl. ..... Plt./317
(58) Field of Search ..... Plt./317

*Primary Examiner*—Bruce R. Campell
*Assistant Examiner*—Annette H. Para
(74) *Attorney, Agent, or Firm*—Foley & Lardner

(57) ABSTRACT

A new and distinct Impatiens plant named 'Danchesparkrd' characterized by having compact growth habit; small flowers; small, green leaves; trailing growth habit; and red flowers.

1 Drawing Sheet

Latin name of the genus and species of the plant claimed: *Impatiens walleriana.*
Variety denomination: Danchesparkrd.

BACKGROUND OF THE INVENTION

The present invention relates to a new and distinct cultivar of Impatiens plant, botanically known as *Impatiens walleriana,* hereinafter referred to by the cultivar name 'Danchesparkrd'.

The new cultivar originated from a cross made in a controlled breeding program in Moshav Mishmar Hashiva, Israel. The female parent is FRB-100 (unpatented, proprietary cultivar). The male parent is BGA-10 (unpatented, proprietary cultivar). 'Danchesparkrd' was discovered and selected by the inventor, Gabriel Danziger, as a flowering plant within the progeny of the stated cross in a controlled environment in Moshav Mishmar Hashiva, Israel.

Asexual reproduction of the new cultivar by leaf cutting was first performed in April, 1999 in Moshav Mishmar Hashiva, Israel and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danchesparkrd' which in combination distinguish this Impatiens as a new and distinct cultivar:

1. Compact growth habit;
2. Small flowers;
3. Small, green leaves;
4. Trailing growth habit; and
5. Red flowers.

'Danchesparkrd' has not been observed under all possible environmental conditions. The phenotype of the new cultivar may vary significantly with variations in environment such as temperature, light intensity, and daylength without any change in the genotype of the plant.

Of the many commercial cultivars known to the present inventor, the most similar in comparison to 'Danchesparkrd' is cultivar 'Firefly Red'.

TABLE 1

| | 'Danchesparkrd' | Firefly Red |
|---|---|---|
| Flower Color-upper surface | RHS 42A | RHS 45C |
| Leaf Color-Upper surface | RHS 137C | RHS 137C |
| Flower Size | 2.5 cm | 2.5 cm |

BRIEF DESCRIPTION OF THE DRAWING

The accompanying photographic drawing illustrates the overall appearance of the new Impatiens showing the colors as true as is reasonably possible with colored reproductions of this type. The drawing shows a whole plant side-view of a flowering potted 'Danchesparkrd' plant.

DETAILED BOTANICAL DESCRIPTION

The following observations, measurements and values describe the new cultivar as grown in Moshav Mishmar Hashiva, Israel under conditions which closely approximate those generally used in commercial practice. The plant was grown in a greenhouse under the typical Israeli weather conditions (Winter night time temperature 18° C., winter day time temperature 20–25° C.; summer night time temperature approximately 25° C., summer day time temperature approximately 30° C.). Fertilization: N: P: K=5:3:8, N=100 ppm.

Color references are made to The Royal Horticultural Society Colour Chart (R.H.S.) except where general colors of ordinary significance are used. Color values were taken under daylight conditions at approximately noon in Moshav Mishmar Hashiva, Israel. The age of the plant described is 13 weeks from planting. Propagation was done by leaf cutting.

Plant:

*General appearance and form.*—Height: Approximately 15 cm. Plant spread: Trailing, 32 cm.

*Lateral branches.*—Length 15–18 cm, internode length approximately 4–4.5 cm; diameter 0.5 cm; branch color R.H.S. 139D; anthocyanin color RHS 184A.
*Flowering response.*—Flowers at any day length.
*Flowering season.*—Year round.
*Winter hardiness.*—Resistance to 10° C.
*Lastingness of the individual bloom.*—About 15 days.
*Rooting habit.*—Adventitious roots from cutting base.
*Time to initiate roots.*—10 days.
*Time to produce a rooted cutting or liner.*—17 days.
*Growth and branching habit.*—Trailing type, strong branching.
*Crop time.*—10 weeks after planting in a 10–12 cm pot.
*Fragrance.*—None.

Foliage:
*Apex.*—Acuminate.
*Base.*—Acute.
*Length.*—Approximately 2.5 cm.
*Width.*—Approximately 2.5 cm.
*Margin.*—Shallowly Serrate.
*Texture.*—Smooth.
*Color of upper surface.*—Mature leaf: R.H.S. 137C. Immature leaf: R.H.S. 137B.
*Color of lower surface.*—Mature leaf: R.H.S. 147C. Immature leaf: R.H.S. 147D.
*Venation.*—None.
*Petiole.*—Length: Approximately 1–1.5 cm. Diameter: 2 mm. Color: R.H.S. 145C.

Inflorescence:
*Flower type and habit.*—Single flower, day neutral.
*Flower diameter.*—2.5 cm.
*Overall shape.*—Irregular — 5 petaled.
*Average number of flowers per lateral branch.*—Approximately 5–7.
*Petals.*—Petal Number: 5. Petal Shape: Spatulate. Texture: Smooth. Petal size: Length about 1.2 cm; width about 0.8 cm. Petal Color: Upper surface: R.H.S. 42A. Lower surface: R.H.S. 42C.
*Stem.*—Average length: 17 cm. Average diameter: 1 cm. Color: Green, R.H.S. 146C. Internode length: 2 cm.
*Bud.*—Rate of opening: From the emergence of color until anthesis: 2 days. Color: R.H.S. 159B. Shape: Conical. Length: 0.7 cm. Diameter: 0.4 cm.
*Peduncles.*—Length about 2.4 cm; slightly upward angle; stable strength.

Reproductive organs:
*Stamen.*—Number: 5. Color: Purple, R.H.S. 77C.
*Seeds.*—Width: 1 mm. Length: 1 mm. Shape: Lanceolate. Color: Brown, R.H.S. 165A.
*Fruit.*—Color: Green, 144A.
*Anthers.*—Color: 63B.
*Pollen.*—None.
*Stigma.*—Color: Green, R.H.S. 144B.
*Ovary.*—Color: Green, R.H.S. 144B.

Disease resistance: No sensitivity to disease was observed under regular growing conditions.

I claim:

1. A new and distinct Impatiens plant named 'Danchesparkrd', substantially as illustrated and described herein.

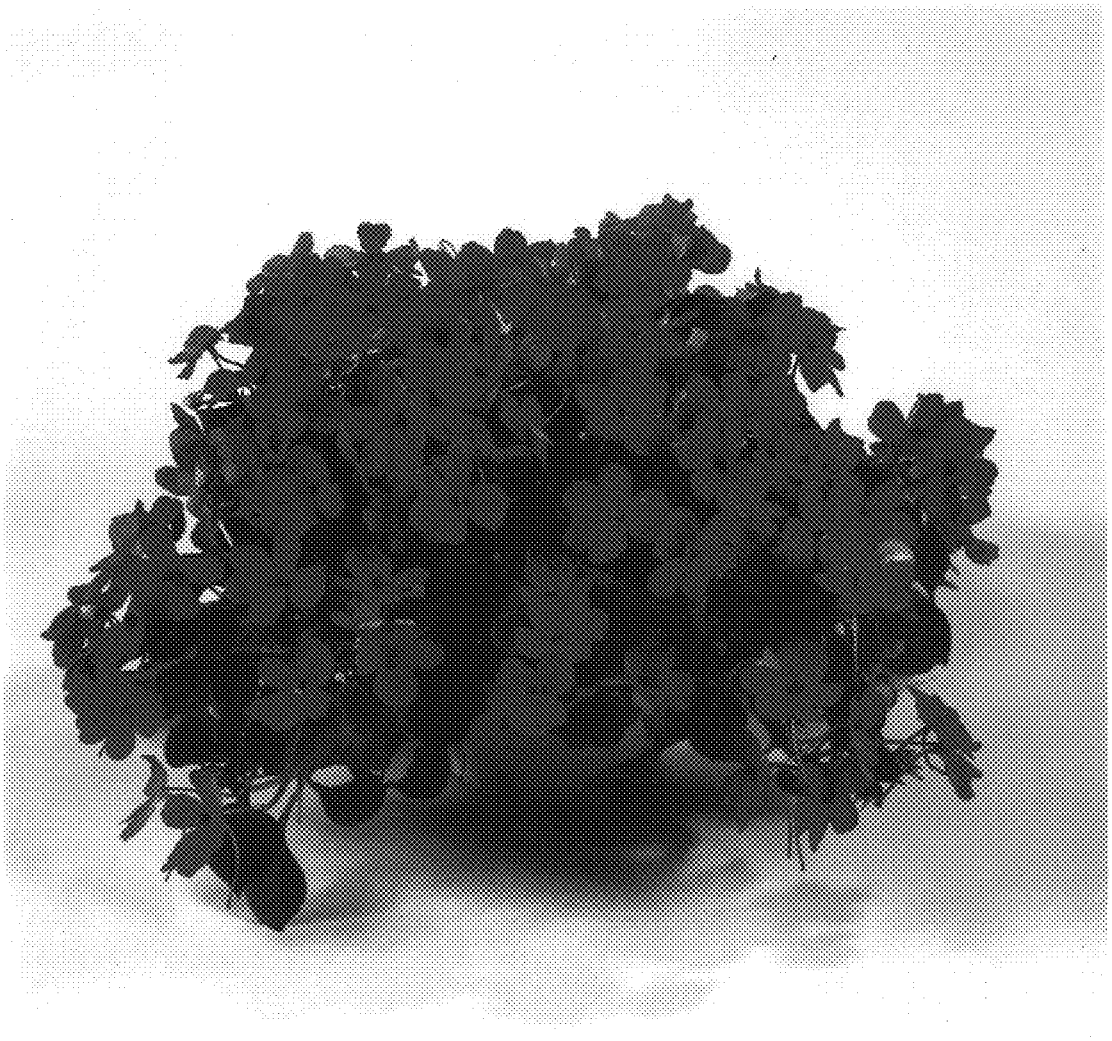

* * * * *